(12) United States Patent
Boehringer et al.

(10) Patent No.: US 7,981,098 B2
(45) Date of Patent: Jul. 19, 2011

(54) SYSTEM FOR SUCTION-ASSISTED WOUND HEALING

(75) Inventors: John R. Boehringer, Wynnewood, PA (US); John Karpowicz, Chester Springs, PA (US); Christopher L. Radl, Malvern, PA (US); Kevin P. Klocek, Ardmore, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 387 days.

(21) Appl. No.: 12/233,211

(22) Filed: Sep. 18, 2008

(65) Prior Publication Data

US 2009/0012501 A1 Jan. 8, 2009

Related U.S. Application Data

(60) Division of application No. 11/226,505, filed on Sep. 14, 2005, now Pat. No. 7,625,362, which is a continuation-in-part of application No. 10/663,226, filed on Sep. 16, 2003, now Pat. No. 7,815,616, said application No. 12/233,211 is a continuation-in-part of application No. 10/663,226, filed on Sep. 16, 2003.

(60) Provisional application No. 60/625,896, filed on Nov. 8, 2004, provisional application No. 60/410,718, filed on Sep. 16, 2002.

(51) Int. Cl.
*A61F 13/00* (2006.01)
*A61M 1/00* (2006.01)

(52) U.S. Cl. ......... 604/313; 604/304; 604/305; 604/319

(58) Field of Classification Search .................. 604/319, 604/304, 305, 313
See application file for complete search history.

(56) References Cited

U.S. PATENT DOCUMENTS

| | | | |
|---|---|---|---|
| 679,918 A | 8/1901 | Shears |
| 697,637 A | 4/1902 | Lee |
| 720,812 A | 2/1903 | Johnson |
| 843,674 A | 2/1907 | Funk |
| 1,066,934 A | 7/1913 | Manney |
| 1,251,258 A | 12/1917 | Magill |
| 1,355,679 A | 10/1920 | McConnel |
| 1,385,346 A | 7/1921 | Taylor |
| 2,025,492 A | 12/1935 | Aird |

(Continued)

FOREIGN PATENT DOCUMENTS

EP 0619105 A1 10/1994

(Continued)

OTHER PUBLICATIONS

Dewan, An Alternative Approach to Skin Graft Donor Site Dressing, Jun. 1986. 2 pages.

(Continued)

*Primary Examiner* — Melanie Hand
(74) *Attorney, Agent, or Firm* — Caesar, Rivise, Bernstein, Cohen & Pokotilow, Ltd.

(57) ABSTRACT

A system for treating a wound with suction is provided. The system comprises a wound cover, a pump having an input port and an output port, the input port providing suction to the wound via the wound cover, and a reservoir coupled to the output port of the pump. The reservoir is adapted to receive effluent from the wound and the pump is capable of maintaining a controlled level of suction at the wound.

27 Claims, 10 Drawing Sheets

U.S. PATENT DOCUMENTS

| | | | |
|---|---|---|---|
| 2,113,253 A | 4/1938 | Gray |
| 2,122,121 A | 6/1938 | Tillotson |
| 2,195,771 A | 4/1940 | Estler |
| 2,280,915 A | 4/1942 | Johnson |
| 2,367,690 A | 1/1945 | Purdy |
| 2,385,207 A | 9/1945 | Hunn |
| 2,524,750 A | 10/1950 | Bellinger |
| 2,727,678 A | 12/1955 | Henderson |
| 3,026,874 A | 3/1962 | Stevens |
| 3,042,037 A | 7/1962 | Scales |
| 3,042,041 A | 7/1962 | Jascalevich |
| 3,288,140 A | 11/1966 | McCarthy |
| 3,367,332 A | 2/1968 | Groves |
| 3,397,648 A | 8/1968 | Henderson |
| 3,398,743 A | 8/1968 | Shalit |
| 3,486,504 A | 12/1969 | Austin |
| 3,556,096 A | 1/1971 | Fuller |
| 3,568,675 A | 3/1971 | Harvey |
| 3,599,639 A | 8/1971 | Spotz |
| 3,610,238 A | 10/1971 | Rich |
| 3,616,156 A | 10/1971 | Scholl |
| 3,874,387 A | 4/1975 | Barbieri |
| RE28,405 E | 5/1975 | Sollerud |
| 3,933,158 A | 1/1976 | Haverstock |
| 3,954,105 A | 5/1976 | Nordby |
| RE29,319 E | 7/1977 | Nordby et al. |
| 4,080,970 A | 3/1978 | Miller |
| 4,112,947 A | 9/1978 | Nehring |
| 4,180,074 A | 12/1979 | Murry |
| 4,224,941 A | 9/1980 | Stivala |
| 4,224,945 A | 9/1980 | Cohen |
| 4,250,882 A | 2/1981 | Adair |
| 4,261,363 A | 4/1981 | Russo |
| 4,341,208 A | 7/1982 | Gordon |
| 4,382,441 A | 5/1983 | Svedman |
| 4,385,630 A | 5/1983 | Gilcher et al. |
| 4,392,858 A | 7/1983 | George |
| 4,399,816 A | 8/1983 | Spangler |
| 4,444,548 A | 4/1984 | Andersen et al. |
| 4,465,062 A | 8/1984 | Versaggi et al. |
| 4,533,352 A | 8/1985 | Van Beek et al. |
| 4,551,141 A | 11/1985 | McNeil |
| 4,553,967 A | 11/1985 | Ferguson et al. |
| 4,641,643 A | 2/1987 | Greer |
| 4,710,165 A | 12/1987 | McNeil et al. |
| 4,717,382 A | 1/1988 | Clemens |
| 4,743,232 A | 5/1988 | Kruger |
| 4,778,446 A | 10/1988 | Jensen |
| 4,795,435 A | 1/1989 | Steer |
| 4,820,284 A | 4/1989 | Hauri |
| 4,925,447 A | 5/1990 | Rosenblatt |
| 4,930,997 A | 6/1990 | Bennett |
| 4,941,882 A | 7/1990 | Ward |
| 4,969,880 A | 11/1990 | Zamierowaski |
| 4,969,881 A | 11/1990 | Viesturs |
| 4,995,400 A | 2/1991 | Boehringer et al. |
| 5,014,389 A | 5/1991 | Ogilvie |
| 5,019,059 A | 5/1991 | Goldberg et al. |
| 5,034,006 A | 7/1991 | Hosoda |
| 5,086,763 A | 2/1992 | Hathman |
| 5,088,483 A | 2/1992 | Heinecke |
| 5,100,396 A | 3/1992 | Zamierowski |
| 5,106,362 A | 4/1992 | Gilman |
| 5,149,331 A | 9/1992 | Ferdman et al. |
| 5,152,757 A | 10/1992 | Erikson |
| 5,160,315 A | 11/1992 | Heinecke |
| 5,161,544 A | 11/1992 | Morris |
| 5,167,613 A | 12/1992 | Karami |
| 5,176,663 A | 1/1993 | Svedman |
| 5,244,457 A | 9/1993 | Karami |
| 5,261,893 A | 11/1993 | Zamierowaski |
| 5,358,494 A | 10/1994 | Svedman |
| 5,380,308 A | 1/1995 | Gunya et al. |
| 5,437,651 A | 8/1995 | Todd |
| 5,437,683 A | 8/1995 | Neumann |
| 5,447,505 A | 9/1995 | Valentine |
| D364,679 S | 11/1995 | Heaton et al. |
| 5,480,030 A | 1/1996 | Sweeney |
| 5,484,399 A | 1/1996 | DiResta |
| 5,527,293 A | 6/1996 | Zamierowski |
| 5,549,584 A | 8/1996 | Gross |
| 5,562,107 A | 10/1996 | Lavender et al. |
| 5,636,643 A | 6/1997 | Argenta |
| 5,645,081 A | 7/1997 | Argenta |
| 5,701,917 A | 12/1997 | Khouri |
| 5,840,049 A | 11/1998 | Tumey et al. |
| 5,848,998 A | 12/1998 | Marasco, Jr. |
| D406,899 S | 3/1999 | Cottle |
| 5,931,797 A | 8/1999 | Tumey et al. |
| 5,951,533 A | 9/1999 | Freeman |
| 6,045,541 A | 4/2000 | Matsumoto et al. |
| 6,071,267 A | 6/2000 | Zamierowski |
| 6,116,781 A | 9/2000 | Skeens |
| 6,117,111 A | 9/2000 | Fleischmann |
| 6,135,116 A | 10/2000 | Vogel |
| 6,142,982 A | 11/2000 | Hunt et al. |
| 6,174,306 B1 | 1/2001 | Fleischmann |
| 6,203,563 B1 | 3/2001 | Fernandez |
| 6,242,665 B1 | 6/2001 | Malowaniec |
| 6,283,931 B1 | 9/2001 | Augustine |
| 6,323,386 B1 | 11/2001 | Stapf et al. |
| 6,345,623 B1 | 2/2002 | Heaton et al. |
| 6,436,078 B1 | 8/2002 | Svedman |
| 6,458,109 B1 | 10/2002 | Henley et al. |
| 6,537,033 B2 | 3/2003 | Brazil et al. |
| 6,553,998 B2 | 4/2003 | Heaton et al. |
| 6,557,704 B1 | 5/2003 | Randolph |
| 6,626,891 B2 | 9/2003 | Ohmstede |
| 6,685,681 B2 | 2/2004 | Lockwood et al. |
| 6,695,823 B1 | 2/2004 | Lina et al. |
| 6,755,807 B2 | 6/2004 | Risk, Jr. et al. |
| 6,764,462 B2 | 7/2004 | Risk, Jr. et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 6,998,511 B2 | 2/2006 | Worthley |
| 7,004,915 B2 | 2/2006 | Boynton et al. |
| 7,022,113 B2 | 4/2006 | Lockwood et al. |
| 7,077,832 B2 | 7/2006 | Fleischmann |
| 7,128,735 B2 | 10/2006 | Weston |
| 7,195,624 B2 | 3/2007 | Lockwood et al. |
| 7,216,651 B2 | 5/2007 | Argenta |
| 7,284,965 B2 | 10/2007 | Adahan |
| 7,553,306 B1 | 6/2009 | Hunt et al. |
| 2001/0020146 A1 | 9/2001 | Satterfield |
| 2001/0031943 A1 | 10/2001 | Urie |
| 2001/0043943 A1 | 11/2001 | Coffey |
| 2002/0143286 A1 | 10/2002 | Tumey |
| 2003/0093041 A1 | 5/2003 | Risk, Jr. et al. |
| 2003/0219469 A1 | 11/2003 | Johnson et al. |
| 2004/0002670 A1 | 1/2004 | Mothersbaugh et al. |
| 2004/0006319 A1 | 1/2004 | Lina et al. |
| 2004/0064132 A1 | 4/2004 | Boehringer et al. |
| 2005/0215961 A1 | 9/2005 | Romano et al. |
| 2007/0167927 A1 | 7/2007 | Hunt et al. |
| 2009/0264837 A1 | 10/2009 | Adahan |

FOREIGN PATENT DOCUMENTS

| | | |
|---|---|---|
| EP | 0853950 A1 | 7/1998 |
| EP | 0777504 B1 | 10/1998 |
| GB | 1395799 | 5/1975 |
| GB | 1549756 | 8/1979 |
| GB | 2099308 A | 12/1982 |
| GB | 2307180 A | 5/1997 |
| GB | 2329127 A | 3/1999 |
| GB | 2336546 A | 10/1999 |
| GB | 2333965 A | 11/1999 |
| GB | 2351025 A | 12/2000 |
| GB | 2356148 A | 5/2001 |
| GB | 2365350 A | 2/2002 |
| WO | 8001139 A1 | 6/1980 |
| WO | 8905133 A1 | 6/1989 |
| WO | 9100718 A1 | 1/1991 |
| WO | 9605873 A1 | 2/1996 |
| WO | WO 9605873 A1 * | 2/1996 |
| WO | 9718007 A1 | 5/1997 |
| WO | 9817329 A1 | 4/1998 |

| WO | 0021586 A1 | 4/2000 |
| WO | 0059418 A1 | 10/2000 |
| WO | 0059424 A1 | 10/2000 |
| WO | 0134223 A1 | 5/2001 |
| WO | 0137922 A1 | 5/2001 |
| WO | 0185248 A1 | 11/2001 |
| WO | 03016719 A1 | 2/2003 |
| WO | 03057070 A2 | 7/2003 |
| WO | 2004037334 A1 | 5/2004 |

OTHER PUBLICATIONS

Alexander, Bacteriologic Comparison of Closed Suction and Penrose Drainage, Nov. 1984. 1 Page.
Genecov, A Controlled Subatmospheric Pressure Dressing Increases the Rate of Skin Graft Donor Site Reepithelialization, Mar. 1998. 7 pages.
Biblehimer, Dealing with a Wound that Drains 1.5 Liters a Day, Aug. 1986. 3 Pages.
Fay, Drainage Systems: Their Role in Wound Healing, Sep. 1987. 10 Pages.
Fredman, Dressing System Providing Fluid Supply and Suction Drainage Under for Continuous or Intermitent Irrigation, Aug. 1986. 8 Pages.
Morykwas, Effects of Varying Levels Subatmospheric Pressure on the Rate of Granulation Tissue Formation in Expermintal Wounds in Swine, Nov. 2001. 5 Pages.
Alexander, Emerging Concepts in the Control of Surgical Infections, Jun. 1974. 13 Pages.
Hathman Medical Products, 1 Page.
Pescovitz, A History of Surgical Suction from Dieulafoy to Gomco, Sep. 1989. 9 Pages.
Fowler, How to Cope When Your Patient Has an Enterocutaneous Fistula, Mar. 1980. 4 Pages.
Landes, An Improved Suction Device for Draiing Wounds, May 1972. 1 Page.
Svedman, Irrigation Treatment of Leg Ulcers, Sep. 1983. 3 Pages.
Jeter, Managing Draining Wounds and Fistulae: New and Established Methods; , 1990. 7 Pages.
Shaer, Inexpensive Vacuum-Assisted Closure Employing a Conventional Disposable Closed-Suction Drainage System, Jan. 2003. 2 Pages.
Arnljots, Irrigation Treatment in Split-Thickness Skin Grafting of Intractable Leg Ulcers, 1985. 3 pages.
Nakayama, A New Method for the Dressing of Free Skin Grafts, Dec. 1990. 4 Pages.
Rabinovici, New Sump Suction Appliance for Drainage of Enterocutaneous Fistulae, May 1988, 1 Page.
Abramson, A New, Soft, Triple Lumen, Overflow and Suction Drain, Sep. 1970. 3 Pages.
Ramirez, Opimal Wound Healing Under Op-Site Dressing, Mar. 1973. 2 Pages.
Bellinger, An Original Drainage Cup Apparatus for Ileostomies and Fistullas, Nov. 1949. 5 Pages.
Alexander, Prevention of Wound Infections—A Case for Closed Drainage to Remove Wound Fluids Deficient in Opsonic Proteins, Jul. 1976. 5 Pages.
Gramm, Respitory Controlled Intermittent Inspiratory Pleural Drainage, Oct. 1984. 1 Page.
Schein, The "Sandwich Technique" in the Management of the Open Abdonmen, May 1986. 2 Pages.
Akira, Sternal Dehiscense: "Delayed Primary Closure" for Complicated Cases, 1981. 3 Pages.
Hentzer, Suction Blister Transplantation for Leg Ulcers, 1975. 3 Pages.
Furnas, Suction Catheters for Open Technique of Skin Grafting in Fresh Wounds, Oct. 1976. 1 Page.
Jascalevich, Suction Cone: A New Apparatus for the Care of Ileostomies, Fistulas and Draining Sinuses, Sep. 1960. 4 Pages
Silvis, The Use of Continuous Suction Negative Pressure Instead of Pressure Dressing, Aug. 1955. 5 Pages
Morykwas, Use of a Subatmospheric Pressure to Prevent Doxorubicin Extravasation Ulcers in a Swine Model, Jun. 1999. 4 Pages.
Morykwas, Use of a Subatmospheric Pressure to Prevent Progression of Partial-Thickness Burns in a Swine Model, Jan. 1999. 7 Pages.
Vieira, Vacuum Assisted Closure in Calcanectomy for the Treatment of Chronic Calcaneal Osteomyelitis, Jun. 1997. 2 Pages.
Barker, Vacuum Pack Technique of Temporary Abdominal Closure: A 7-Year Experience with 112 Patients, Feb. 2000. 6 Pages.
Argenta, Vacuum-Assisted Closure: A New Method for Wound Control and Treatment: Clinical Experience, Jun. 1997. 15 Pages.
Industrial Newsroom (Industrial Specialties Mfg., Inc.) Oct. 26, 2004 web document.
International Search Report for PCT International Application No. PCT/US05/39996, mailing date Jun. 13, 2006.

* cited by examiner

SYSTEM FOR SUCTION-ASSISTED WOUND HEALING

CROSS REFERENCE TO RELATED APPLICATIONS

The present application is a divisional application which claims the benefit under 35 U.S.C. §121 of application Ser. No. 11/226,505, filed on Sep. 14, 2005, which in turn claims the benefit under both 35 U.S.C. §119(e) of Provisional Application Ser. No. 60/625,896 filed on Nov. 8, 2004 and under 35 U.S.C. §120 as a Continuation-in-Part of application Ser. No. 10/663,226 filed on Sep. 16, 2003 which in turn claims the benefit under 35 U.S.C. §119(e) of Provisional Application Ser. No. 60/410,718 filed on Sep. 16, 2002. The present application is also a Continuation-in-Part application which claims the benefit under 35 U.S.C. §120 of application Ser. No. 10/663,226 filed on Sep. 16, 2003, which in turn claims the benefit under 35 U.S.C. §119(e) of Provisional Application No. 60/410,718, filed on Sep. 16, 2002, and all of whose entire disclosures are incorporated herein by reference.

FIELD OF THE INVENTION

The invention relates to a device and method for treating wounds. More specifically, the present invention relates to a device and method for treating wounds with suction.

BACKGROUND OF THE INVENTION

Suction has long been employed in the management of surgical wounds. Closed suction systems are employed to evacuate the wound space and carry potentially deleterious materials away from the patient and to control swelling. Suction has also been employed in the care of open, chronic wounds or hard to heal wounds such as pressure sores.

Basic cellular functions, such as oxygen transport and cellular transduction signaling, are carried out at the capillary level. Chronic wounds such as pressure sores or bed sores are, by definition, a result of poor or impaired circulation and contain ischemic and necrotic tissues. It is desirable to stimulate circulation in the underlying wound tissue through the use of suction.

SUMMARY OF THE INVENTION

In order to overcome the deficiencies of conventional systems, a first exemplary embodiment of the present invention provides a system for treating a wound with suction. The exemplary system includes a wound cover, a pump having an input port and an output port with the input port providing suction to the wound via the wound cover, and a reservoir coupled to the output port of the pump and adapted to receive effluent from the wound.

According to another aspect of the present invention, the pump may be adapted to function during transport.

According to still another aspect of the present invention, the pump comprises an internal power source.

According to yet another aspect of the present invention, the reservoir can be a rigid container or a flexible bag formed from a polymeric film sealed substantially along a perimeter. The reservoir comprises a vent with a membrane to release gases while retaining waste materials.

According to still another aspect of the present invention, the reservoir further comprises a sensing means that determines when the collection means contains a predetermined quantity of effluent.

According to a further aspect of the present invention, a feedback means provides a feedback signal from the wound via the wound cover to the pump.

According to still a further aspect of the present invention, the feedback signal is indicative of a suction level beneath the wound cover.

According to yet another aspect of the present invention, a comparator circuit is coupled to the sensing means for determining the suction level beneath the wound cover.

According to yet a further aspect of the present invention, the pump comprises a controller.

According to still a further aspect of the present invention, the controller outputs a control signal to the pump to control operation of the pump, a state of the control signal based at least in part on the feedback signal. The control signal can also have at least two states corresponding to a pump operating speed and a pump idling or off speed. The control circuit can be further adapted to produce a first alarm signal and/or conduct a system shutdown in response to a predetermined condition of the feedback signal.

According to yet another aspect of the present invention, the feedback means comprises a lumen adapted to conduct a negative pressure from the cover to the pump means.

According to yet a further aspect of the present invention, the feedback means is adapted to receive a fluid to at least partially purge wound effluent from the feedback means.

According to yet another aspect of the present invention, the feedback means is adapted to conduct an infusion fluid to the wound.

According to still another aspect of the present invention, the infusion fluid is selected from the group consisting of saline, an antiseptic, an antibiotic, an analgesic, an anesthetic, and an anti-inflammatory.

According to still a further aspect of the present invention, the infusion fluid may be warmed or chilled to provide a desired therapeutic benefit.

According to yet another aspect of the present invention, the pump delivers the infusion fluid by positive pressure.

According to yet another aspect of the present invention, the pump is adapted to operate between a maximum speed and second speed responsive to pressure at the wound.

According to yet another aspect of the present invention, a change between the maximum speed and the second speed has a gradual profile.

According to yet another aspect of the present invention, a change between the second speed and a further operating speed of the pump has a gradual profile.

According to yet another aspect of the present invention, the system further comprises a wound contact material adapted to be placed beneath the wound cover and in intimate contact with at least one wound surface.

According to yet another aspect of the present invention, the system further comprises a collapsible wound packing material adapted to be placed between the wound cover and the wound contact material.

According to yet another aspect of the present invention, an effluent pressure line is coupled between the pump and the reservoir.

According to yet another aspect of the present invention, the system comprises a wound cover; a detector coupled to the wound cover to receive a signal representative of a level of suction at the wound; a regulator for regulating suction and coupled to the source of suction and the detector; a wound effluent container having first port coupled to the regulator and an effluent input port coupled to the wound cover, such that wound effluent is received via said effluent input port.

According to yet another aspect of the present invention, the suction is provided from a pre-existing in-house suction system.

According to still another aspect of the present invention, the detector compares a level of suction present at the wound with a level of suction output from the controller and generates a signal to the controller responsive to said comparison.

According to yet another aspect of the present invention, the system comprises cover means for covering the wound; pump means for at least generating the suction first coupling means for providing the suction to the wound cover from the pump means; collection means for collecting wound effluent via the wound cover; second coupling means for providing the wound effluent from the pump means to the collection means; and feedback means for providing a feedback signal from the cover means to the pump means.

According to yet another aspect of the present invention, the system comprises a wound cover; a container having at least one resilient portion, the container adapted to at least generate the suction and receive wound effluent; a conduit coupled between the wound cover and the container for providing the suction to the wound and extracting the wound effluent, wherein the suction is generated upon successive compression and release of a portion of the container, such that at least a portion of the gas in the resilient container is expelled from the resilient container upon compression and the suction is generated upon re-expansion of the resilient container to maintain a controlled a level of suction at the wound.

According to yet another aspect of the present invention, the container comprises a first member forming a first face of the container; a second member forming a second face of the container, the first and second members coupled to one another such that the second member can articulate with respect to the first member; a resilient member coupled between the first member and the second member; and a first check valve disposed in the container to expel gasses from the container upon compression of the container and prevent entry of gases into the container upon expansion of the container.

According to yet another aspect of the present invention, a second check valve is coupled between the container and the wound cover to permit flow of wound effluent from the wound to the container back and prevent the flow of gases from the container to the wound cover.

According to yet another aspect of the present invention, a medical waste collection container having a body portion defining an interior space comprises vent means for venting gases from the interior space while retaining waste materials.

These and other aspects will become apparent in view of the detailed description of the invention provided below.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following Figures.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
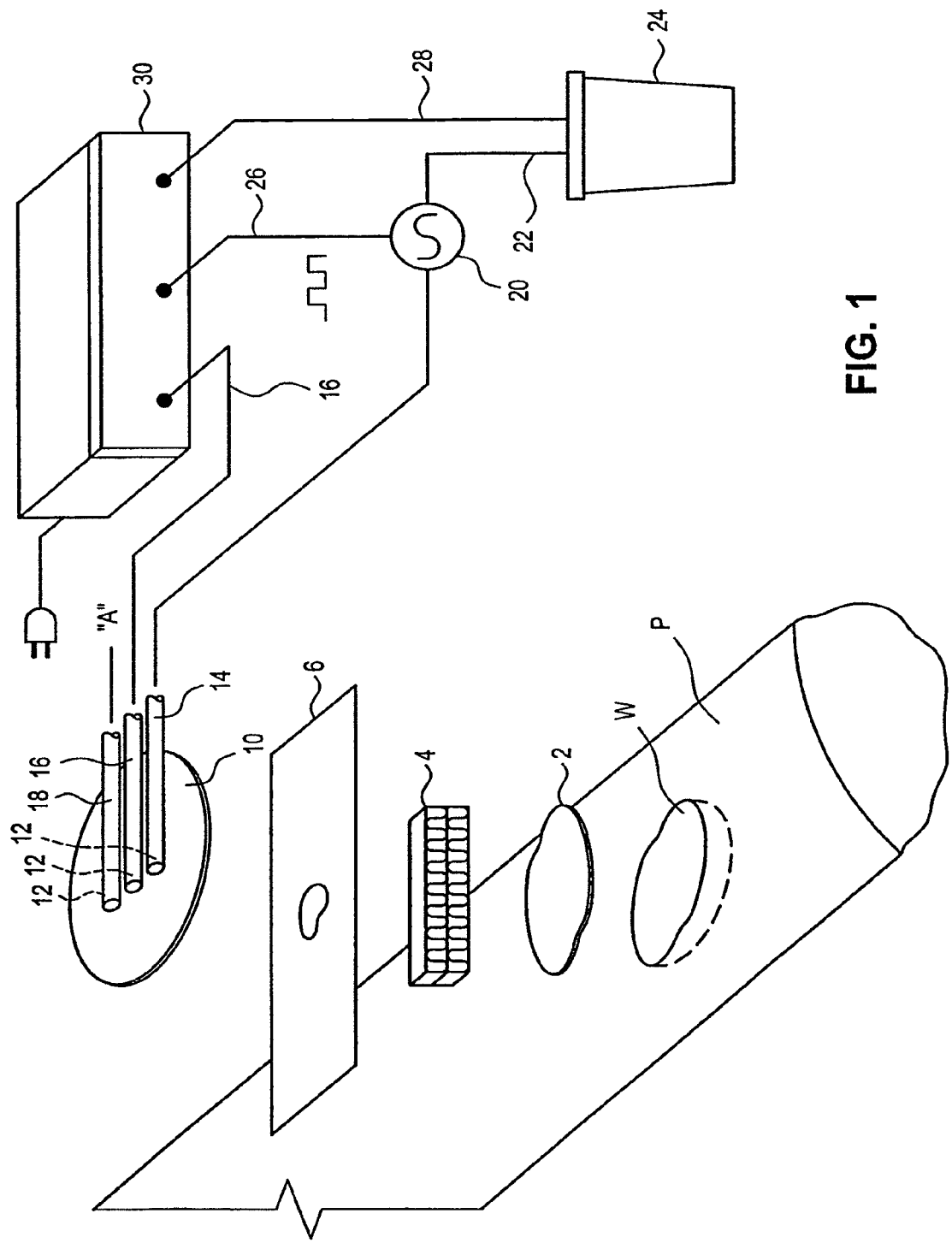
FIG. 1 is a diagram of a system for treating wounds with suction according to a first exemplary embodiment of the present invention.

Referring to FIG. 1, an exemplary system 1 for treating wounds with suction is shown. As illustrated in FIG. 1, wound W is on patient P. Building up from wound W, wound contact layer 2, which can be cut to fit the dimensions of wound W, is placed in intimate contact with one or more surfaces of wound W. Contact layer 2 is desirably formed from one or more permeable materials and is adapted to permit the underlying tissue to breathe as well as conduct fluids away from the wound surface. It is also desirable that the contact layer 2 maintains its modulus of compressibility in the presence of moisture. Such a suitable contact layer is described in U.S. patent application Ser. No. 10/982,346 filed Nov. 4, 2004, which is incorporated herein by reference. For a wound that defines a substantial void, a suitable wound packing material 4 may be introduced into the wound above contact layer 2 to fill the wound void and assist in fluid removal. Wound packing material 4 is desirably formed from a minimally absorbent material and has a resiliently compressible structure adapted to conduct fluids away from the wound surface. It is also desirable that the packing material 4 maintains its modulus of compressibility in the presence of moisture. Such a suitable wound packing material is described in U.S. patent application Ser. No. 10/981,119 filed Nov. 4, 2004, which is incorporated herein by reference.

Wound W is then covered and sealed by wound cover 6 which is desirably formed from a semi-permeable membrane adapted to permit transmission of oxygen and water vapor. At least a portion of wound cover 6 incorporates a pressure sensitive adhesive suitable for repeated attachment and detachment from the patient's skin, as is common in a clinical setting that requires routine inspection of underlying wound W. Application of wound cover 6 isolates the wound from environmental contaminants while permitting the wound to breathe, and also forms a substantially gas tight seal under which therapeutic suction may be applied. It is desirable if wound cover 6 is recloseable, thereby allowing the caregiver to tend to the wound as needed without the patient needing to repeatedly sustain the rigors of placement and removal of pressure sensitive adhesive materials. A suitable recloseable wound cover is described in U.S. Provisional Patent Application No. 60/625,819 filed Nov. 8, 2004, which is incorporated herein by reference.

Figure 2:
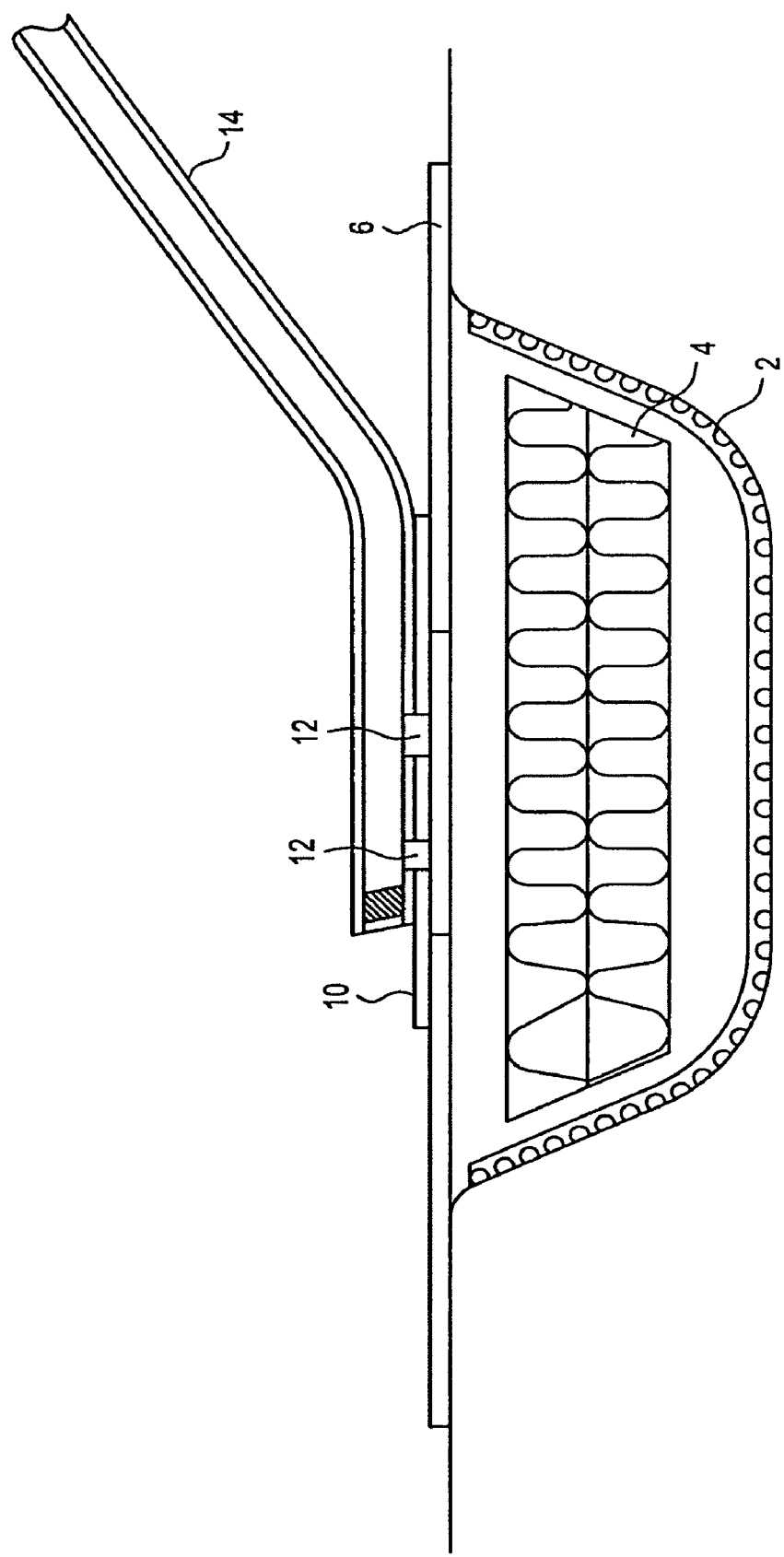
FIG. 2 is a cross sectional view illustrating an exemplary wound interface portion of the present invention.

Suction delivery patch 10 is used to apply suction to the sealed space surrounding wound W. A suitable suction delivery patch 10 is described in U.S. Provisional Patent Application No. 60/625,880 filed Nov. 8, 2004, which is incorporated herein by reference. Suction delivery patch 10 is coupled to suction conduit 14. The interface between delivery patch 10 and suction conduit 14 includes one or more apertures 12 (best shown in FIG. 2) for transmitting suction to the wound space and removing effluent (fluids and other waste materials) from the wound space. Suction conduit 14 may take the form of any lumen suitable for conducting the mostly liquid wound effluent away from the wound space. A flexible medical-grade tubing is typically suitable. The use of various types of conduit are contemplated including a ribbon-type tubing having a reduced profile, which may be desirable depending upon the geometry of the assembly. Suction conduit 14 communicates with pump 20 (discussed further below) which in-turn provides suction to wound W via delivery patch 10.

Referring again to FIG. 1, suction delivery patch 10 is also coupled to one end of a sensing conduit 16. Sensing conduit 16, like suction conduit 14, may take the form of any suitable lumen for transmitting negative pressure. The internal diameter of sensing conduit 16 may be comparatively smaller to that of suction conduit 14, because it is not intended to conduct wound effluent. In this exemplary embodiment, sensing conduit 16 is coupled to controller 30 (discussed further below) which is adapted to read the suction pressure of sensing conduit 16 and therefore the suction pressure at wound W.

In one exemplary embodiment, a sensor (not shown), such as a mechanical or electrical pressure transducer, may be provided as part of delivery patch 10. In such an embodiment, the signal generated by the transducer is provided to controller 30, rather than the direct pneumatic signal from delivery patch 10.

In another exemplary embodiment of the present invention, sensing conduit 16 passively transmits the suction pressure at wound W to the controller 30. In this embodiment, controller 30 comprises an appropriate pressure sensor or converter to convert the pneumatic signal into an electrical signal useful for the controller, and upon which control of the system may be based. In a further exemplary embodiment of the present invention, sensing conduit 16 may be kept free of wound effluent undesirably aspirated into its passage by being fitted with a filter, check valve, and/or being designed to receive a low volume rinsing flow of a sterile fluid or gas.

Figure 3:
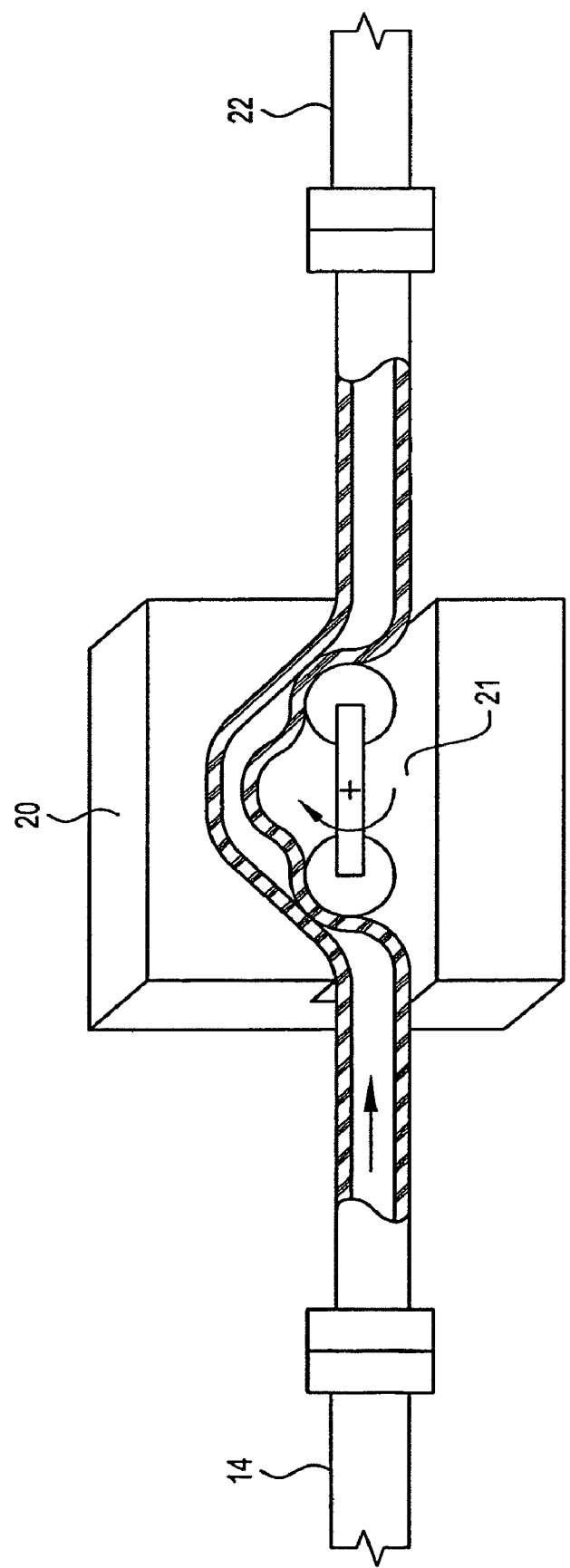
FIG. 3 is a perspective view of a peristaltic pump suitable for use in an exemplary embodiment of the present invention.

Pump 20 employed in the exemplary system may be one of any number of pump types known in the art. One such type is positive displacement pump, such as a peristaltic pump (best shown in FIG. 3), wherein suction conduit 14 is coupled to pump 20. Peristaltic pumps are well known in the art as being capable of pumping a wide array of materials and to be tolerant to debris. Peristaltic pumps are cost effective in that they only require a short length of tubing as a working element for conveying fluids. Peristaltic pumps also isolate other elements from the fluids being conveyed and they are readily interfaced with control systems. Peristaltic pump head 21 will deliver waste materials to collection receptacle 24 (further discussed below).

Figure 8:
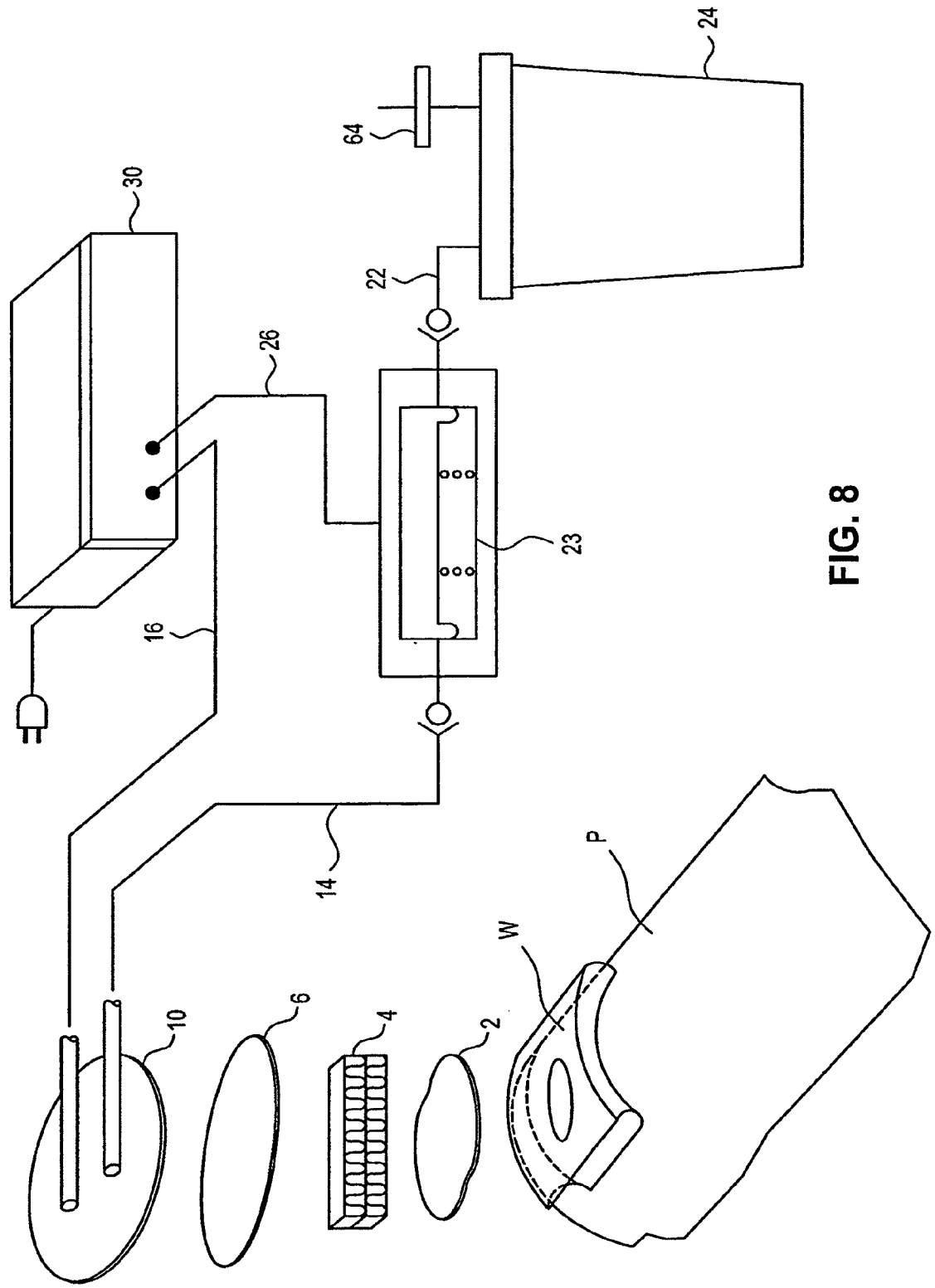
FIG. 8 is a diagram of a system for treating wounds with suction according to a another embodiment of the present invention incorporating a diaphragm pump.

Other pumping systems are readily applied to this system, such as, for example, a diaphragm style pump 23 as illustrated in FIG. 8 may be employed. A diaphragm pump is desirably driven by signal 26 from controller 30. Signal 30 may be in the form of a positive pressure pulse, a negative pressure pulse, a mechanical force or an electrical signal, for example.

Figure 4:
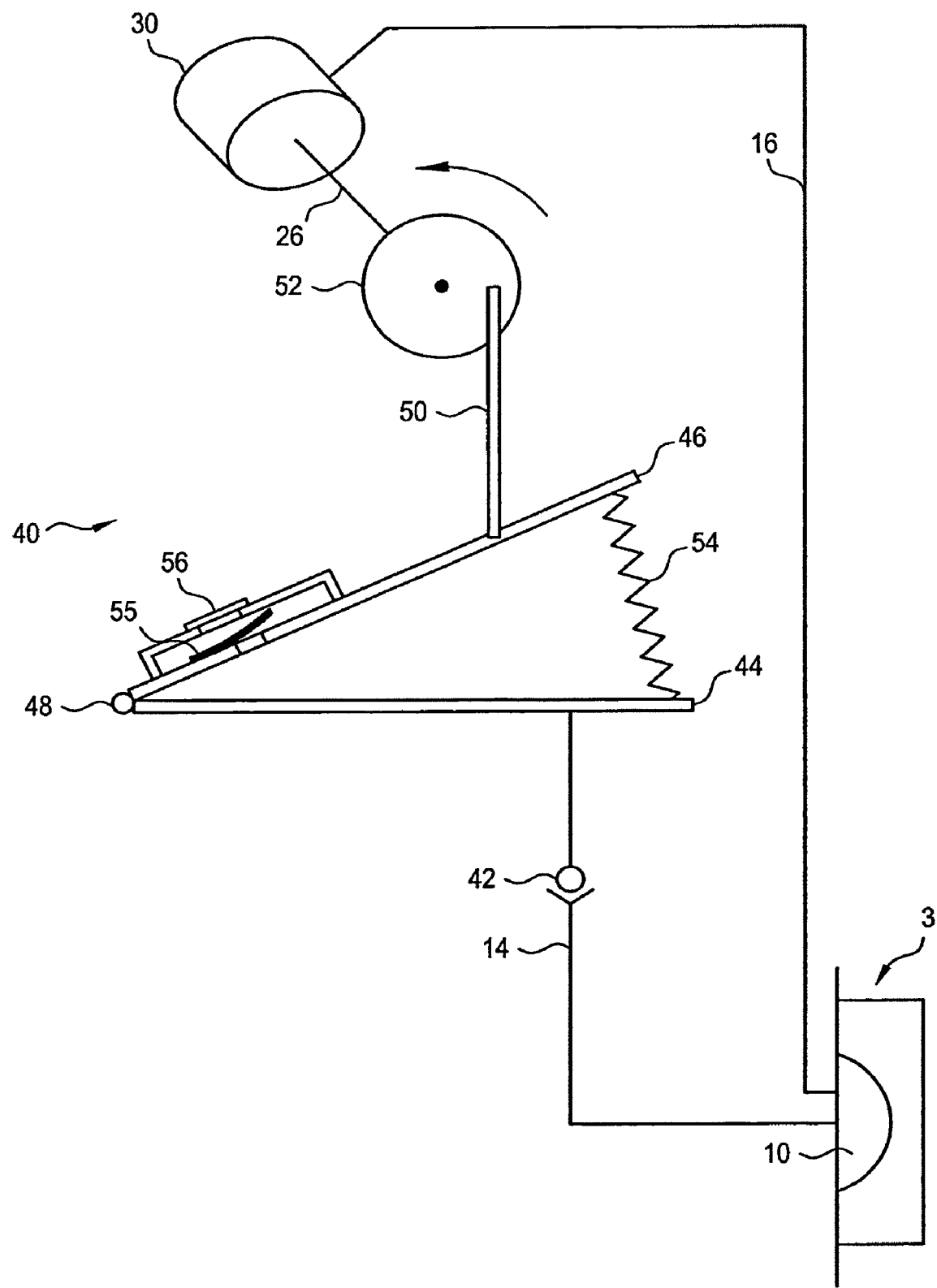
FIG. 4 is an illustration of a system for treating wounds with suction according to another exemplary embodiment of the present invention.

In another exemplary embodiment of the present invention, as illustrated in FIG. 4, a bellows type device 40 may incorporate both the pump and collection receptacle (hereinafter referred to as pump/receptacle 40). In this system, suction conduit 14 is coupled between pump/receptacle 40 and wound W via suction delivery patch 10. Here, suction conduit 14 may also desirably include check valve 42 to limit the direction of the flow in the conduit to flow away from the wound space. In this way, exhaust of gases from pump/receptacle 40 are not conveyed to the wound. Additionally, sensing conduit 16 is coupled between wound W (again via suction delivery patch 10) and controller 30. Controller 30 is in turn coupled to drive system 52, such as an eccentric drive, to provide signal 26 to drive system 52.

In the embodiment illustrated in FIG. 4, face 44 is substantially stationary. Face 46 is coupled to face 44 at hinge point 48 such that face 46 can articulate about hinge point 48 relative to face 44. Resilient element 54, such as an accordion-style material, for example, is coupled to both face 44 and face 46 and proximate ends portions thereof to form a sealed internal space for the accumulation of waste materials. A portion of face 46 is coupled to eccentric drive 52 by coupling arm 50. In rotation, eccentric drive 52 results in the alternate collapse and expansion of pump/receptacle 40. During collapse, gas is expelled through exit check valve 54 and membrane 56. During expansion, suction is created causing waste materials to be drawn into suction conduit 14 through check valve 42 and to be collected in the open internal space of pump/receptacle 40. This configuration reduces tubing connections and minimizes associated parts. Other types of pumps may be employed such as a vane or piston pump, for example.

As in the previous embodiment, suction is provided to wound W until a desired suction level is reached as determined by the feedback provided to controller 30 via sensing line 16. Once this desired level is reached, controller 30 desirably reduces the rate at which pump/receptacle 40 collapses and expands to what the inventors term a "maintenance" speed. As time progresses, however, the level of suction at wound W is likely to be reduced due to minor leaks in the system or permeability of the wound cover, for example. Accordingly, upon controller 30 determining that the suction at wound W falls below a desired level, controller 30 will increase the speed at which pump/receptacle 40 collapses and expands, thus increasing suction at wound W to the desired level.

Referring again to FIG. 1, in one exemplary embodiment controller 30 provides an output signal 26 to drive pump 20. Output signal 26 is at least in part based on the difference between a predetermined desired suction level and the suction level determined by the system at wound W. A suitable algorithm determines a range of operating parameters to actuate pump 20 to generate and maintain suction in the enclosed wound space surrounding wound W.

Preferably, controller 30 includes one or more algorithms adapted to address different pump rates. One algorithm, upon initial startup of system 1, would signal pump 20 to initiate a relatively rapid "draw-down" speed for quickly evacuating atmospheric pressure from system 1, such as by operating at a maximum speed. A rapid draw-down speed would assist healthcare providers in quickly assessing the integrity of seals surrounding wound W as well as the integrity of the remainder of system 1. Another algorithm would signal pump 20 to assume an idling "maintenance" speed. This maintenance speed would permit operation continuously, assist in maintaining adequate system suction, and the life of the internal power source, such as a battery (if such an internal power source is employed) by reducing the power required to accelerate pump 20 from stop to start.

In another exemplary embodiment, it is contemplated that after a predetermined period of time after operating at the "maintenance" speed that the pump is turned off until such time as the system determines that the suction at the wound has decreased to a level requiring reactivation of pump 20.

Another exemplary algorithm would signal pump 20 to assume one or more "load" speeds which would increase the pump speed from the "maintenance" speed. Transitions between the various pump speeds would desirably be achieved by a gradual increase and/or decrease. A gradual speed increase and decrease is preferred in order to minimize abrupt noise level changes that are prone to disturb patient P or other room occupants. In one exemplary embodiment, pump 20 can is adapted to accommodate any one or more of the PID modes; that is, a proportional mode, an integral mode and/or a derivative mode.

As is also typical of controllers, numerous control paradigms are contemplated to trigger alarms, provide operational information, perform data logging, etc. In particular, one or more alarms are contemplated. For example, an alarm and/or system shutdown may be triggered when the collection receptacle is filled to a predetermined level, such as full or nearly full. Such a state may be based on one or more of weight, volume or pressure. In one embodiment, a non contact sensing system is contemplated, such as a sensor which determines a fill state of the container based on the capacitance of the container. This capacitance my be determined though the enclosure of the controller, thus permitting the controller to "see" the level in the collection receptacle. A data logging feature is also contemplated whereby a profile of the system's operation over time would be recorded and outputted to a display (not shown). This feature would assist the monitoring of patient treatment and system troubleshooting.

Controller 30 may be electrically powered through onboard batteries or may be plugged in to conventional AC power or a combination of both.

Collection receptacle 24 is illustrated in FIG. 1 as a typical hospital waste-type rigid container with a cap for the attachment of tubing such as suction conduit 22. An advantage of system 1 over similar systems that are designed to deliver suction to a wound through a collection receptacle (i.e., the receptacle is disposed between the pump and the wound) is that in the present invention the collection receptacle can be a flexible bag. Flexible bags are generally convenient for the collection of waste materials due to ease of handling and reduced cost. Numerous ostomy devices employ bags for waste accumulation and are well received in the marketplace. A flexible bag receptacle may be more well suited to patients that need to maintain a degree of portability.

Figure 5:
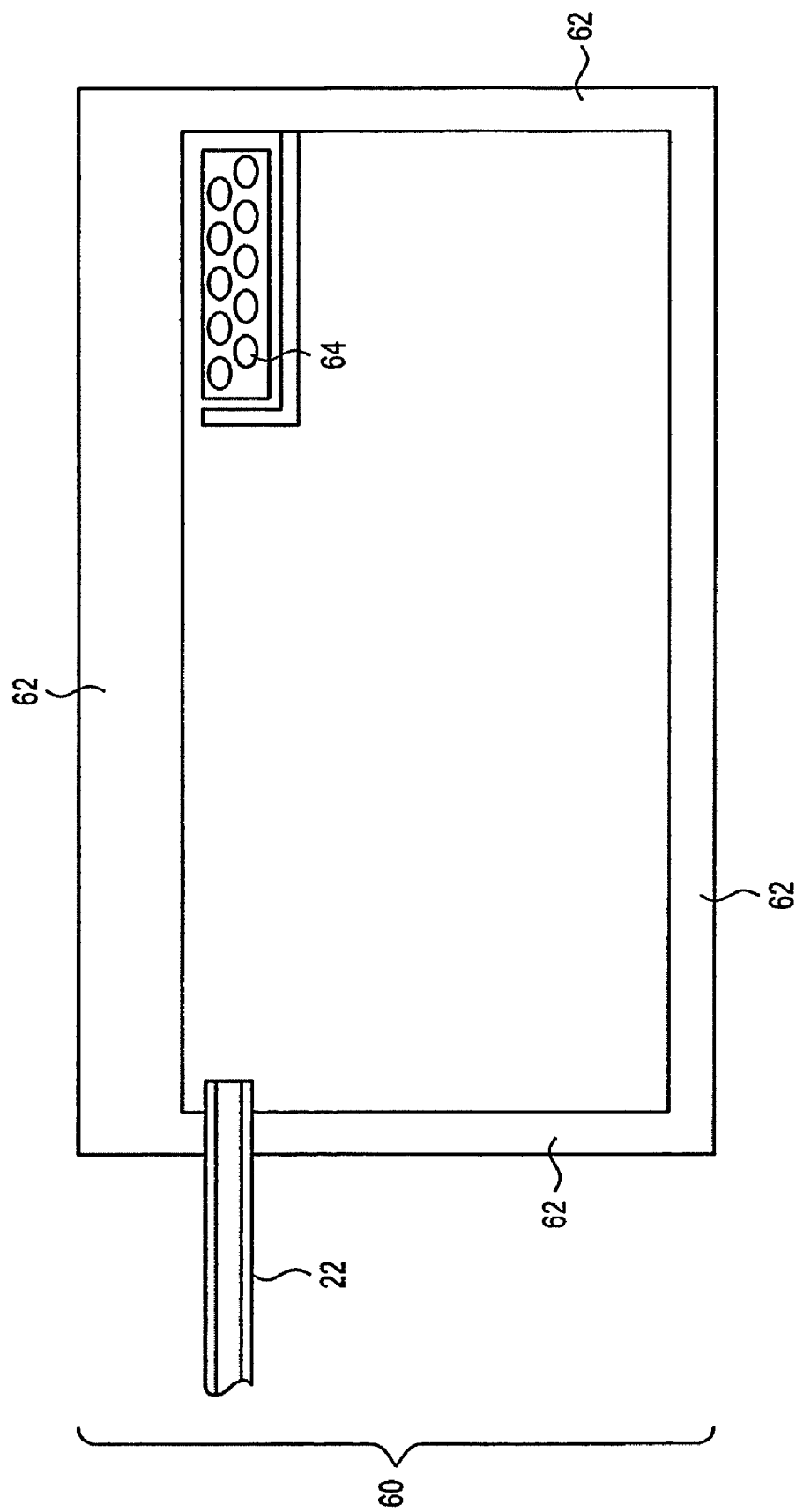
FIG. 5 is a cross sectional view of an effluent collection container of an exemplary embodiment of the present invention.

Thus, as illustrated in FIG. 5, collection receptacle 24 may be a collection bag 60 formed from a rugged polymeric film and sealed by any suitable means known in the art at edges 62. Collection bag 60 is coupled to waste conduit 22 to receive the wound effluent waste stream. Collection bag 60 desirably incorporates a gas discriminating filter 64 for eliminating excess gas from system 1. In order to maintain near atmospheric levels of pressure within receptacle 24, excess gas that might be generated as a result of a leak in any of the system components upstream of the pump 20 can thus be expelled. In the event that gas discriminating filter 64 becomes occluded, it is anticipated that overpressure safety mechanisms (not shown) can be incorporated into collection receptacle 24 to guard against excess fluid removal from the patient.

Figure 6:
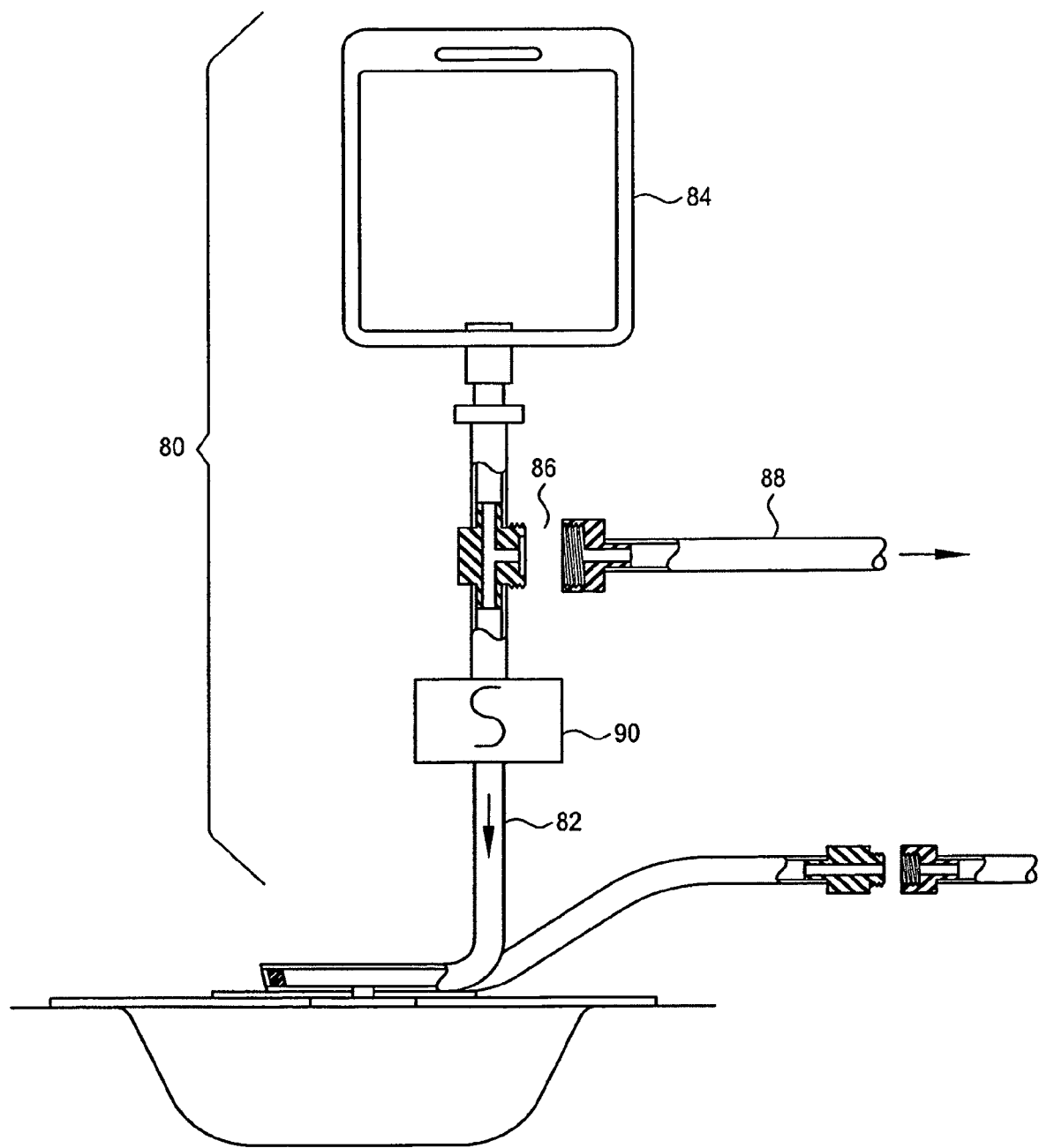
FIG. 6 is an illustration of a fluid infusion portion of an embodiment of the present invention.

In one exemplary embodiment of the present invention, an infusion system 80 as illustrated in FIG. 6 is contemplated for the delivery of one or more therapeutic solutions to wound W. Therapeutic solutions ranging from simple saline to medicated solutions including an antiseptic, antibiotic, analgesic, anti-inflammatory or other suitable pharmaceutically active ingredient are contemplated. Further, these therapeutic solutions may be warmed or chilled for additional therapeutic benefit, as desired. At its distal end, fluid delivery conduit 82 is coupled to suction delivery patch 10 to permit fluid communication beneath delivery patch 10. At its proximal end, fluid delivery conduit 82 is coupled to reservoir 84, such as an I.V. bag. In one embodiment of the present invention, flow from reservoir 84 down through fluid delivery conduit 82 is gravimetric. In one embodiment conduit 84 is equipped with a pressure sensor 86 generally known in the art, such as a electrical transducer or a mechanical transducer. Sensor 86 reads the pressure of delivery conduit 82, which is indicative of the pressure at the wound site, and produces an electrical or mechanical signal which is in-turn provided to controller 30. The therapeutic solutions may also be delivered to the wound responsive to a negative pressure in the wound, thus urging the therapeutic solutions through delivery conduit 82.

Figure 7:
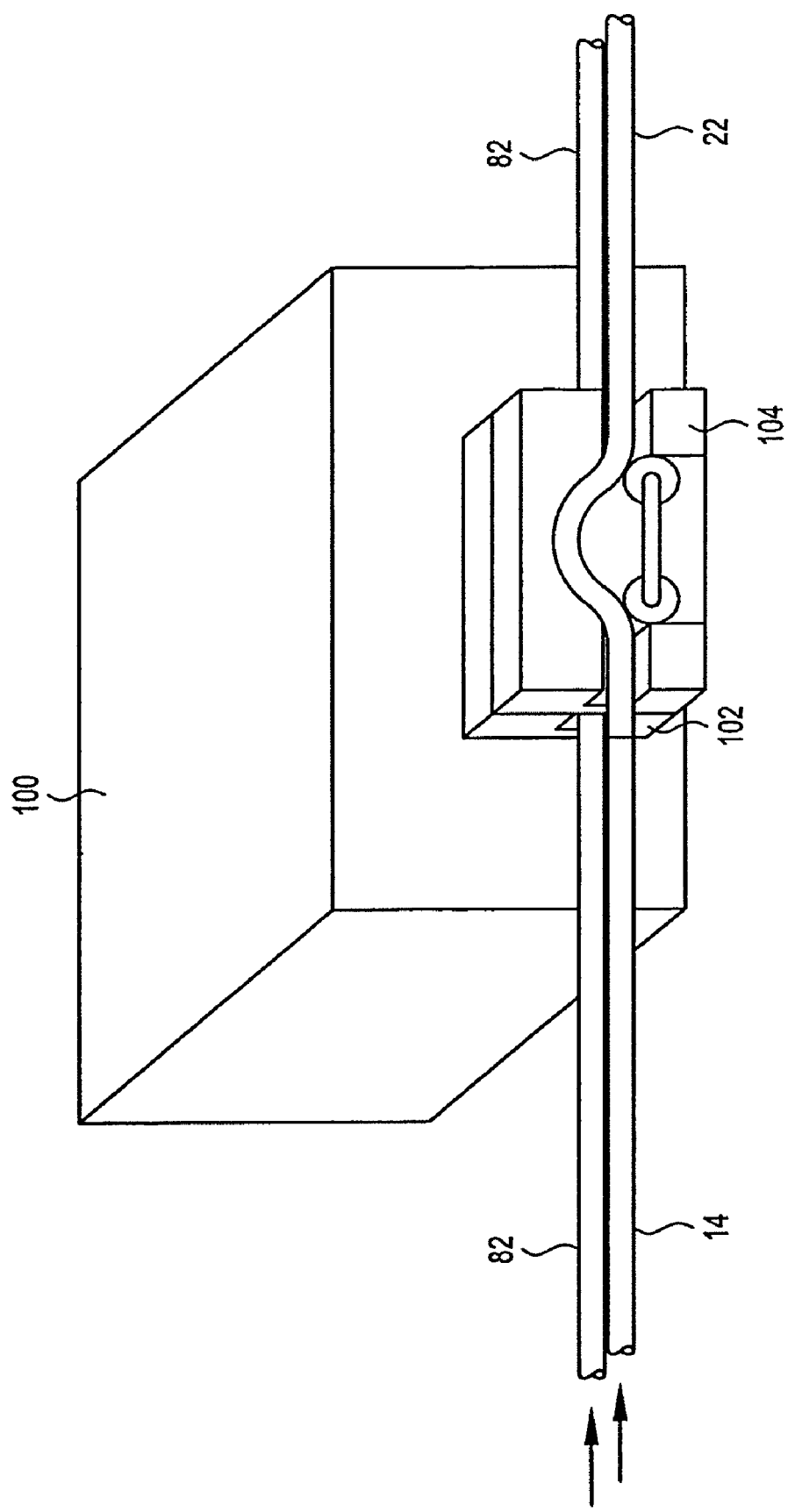
FIG. 7 is a perspective view of another peristaltic pump adapted for use in an embodiment of the present invention.

Alternatively, infusion fluid may be positively delivered through delivery conduit 82 by infusion pump 90 integrated into conduit 82. Pump driven infusion would permit more precise control of the dosing delivered. As with suction pump 20, infusion pump 90 may take the form of any suitable pump design. For the same reasons cited previously for pump 20, infusion pump 90 is preferably a peristaltic pump. Infusion pump 90 can also be coupled to controller 30 to provide pump operation information and to receive control signals similar to those described for suction pump 20. One alternative embodiment of system 1 incorporates a dual head peristaltic pump 100 as shown in FIG. 7. Using dual head peristaltic pump 100, first head 104 performs the function of suction pump 20. In one embodiment, second head 102 substantially simultaneously performs the function of infusion pump 90. This latter embodiment contemplates a single drive mechanism driving first head 104 and second head 102. The invention is not so limited, however, in that two separate drive mechanisms may be employed to drive first head 104 either independently from, or at a different rate than, that of second head 102.

FIG. 8 illustrates a further exemplary system for treating wounds incorporating a diaphragm pump 23 as the means for providing suction to the wound space.

Figure 9:
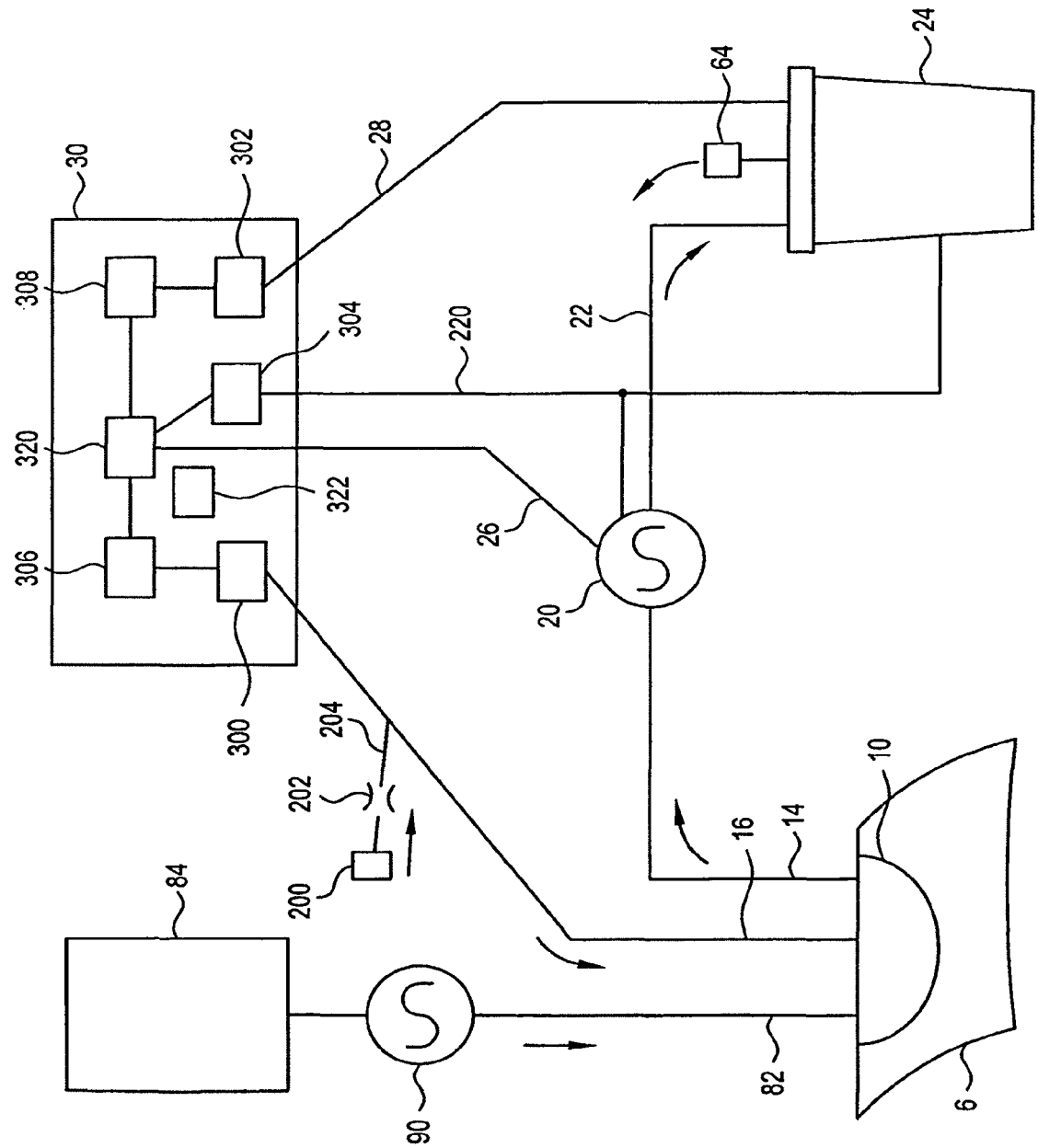
FIG. 9 is a diagram of a system for treating wounds with suction according to a another embodiment of the present invention.

Referring now to FIG. 9, another exemplary embodiment of the preset invention is shown. As illustrated in FIG. 9, a restrictor 202 is coupled to sensing conduit 16 at conduit intersection 204. Filter/inlet 200 is coupled to restrictor 202 to permit an adjustable bleed point for sensing conduit 16. FIG. 9 also illustrates a container sensing line 220 coupled between container 24 and fault detector 304 of controller 30. In one exemplary embodiment, fault detector 304 receives a signal via sensing line 220 indicative of the presence or absence of container 24. Fault detector 304 is coupled to motor controller 320. As discussed above, the stimuli for an alarm or system shutdown can thus be received by controller 30 and subsequently communicated to appropriate system components. Pump 20 is also coupled to container sensing line 220. Coupling pump 20 to sensing line 220 desirably provides a back-up or redundancy to shutdown pump 20 in the event of a container fault. It is recognized that restrictor 202 serves a multitude of purposes: restrictor 202 provides a low-level bias flow whose presence indicates non obstructed operation and will provide positive pressure relief should infusion flow from pump 90 transiently exceed evacuation flow via pump 20.

As illustrated in FIG. 9, controller 30 includes wound pressure receiver 300 coupled to sensing line 16 and logic circuit 306. In turn logic circuit is coupled to motor controller 320. Thus, pressure receiver 300 communicates pressure information from sensing line 16 to logic circuit 306 and on to motor controller 320. Likewise, gas pressure receiver 302 is coupled to gas filled conduit 28. Gas pressure receiver 302 is also coupled to logic circuit 308 which in turn is coupled to motor controller 320. Additionally, it is contemplated that any well-known internal power source 322, such as a battery for example, may be incorporated if desired to provide functionality of controller 30 during transport. As can be appreciated by one skilled in the art, internal power source 322 is coupled to the various subassemblies within controller 30.

Figure 10:
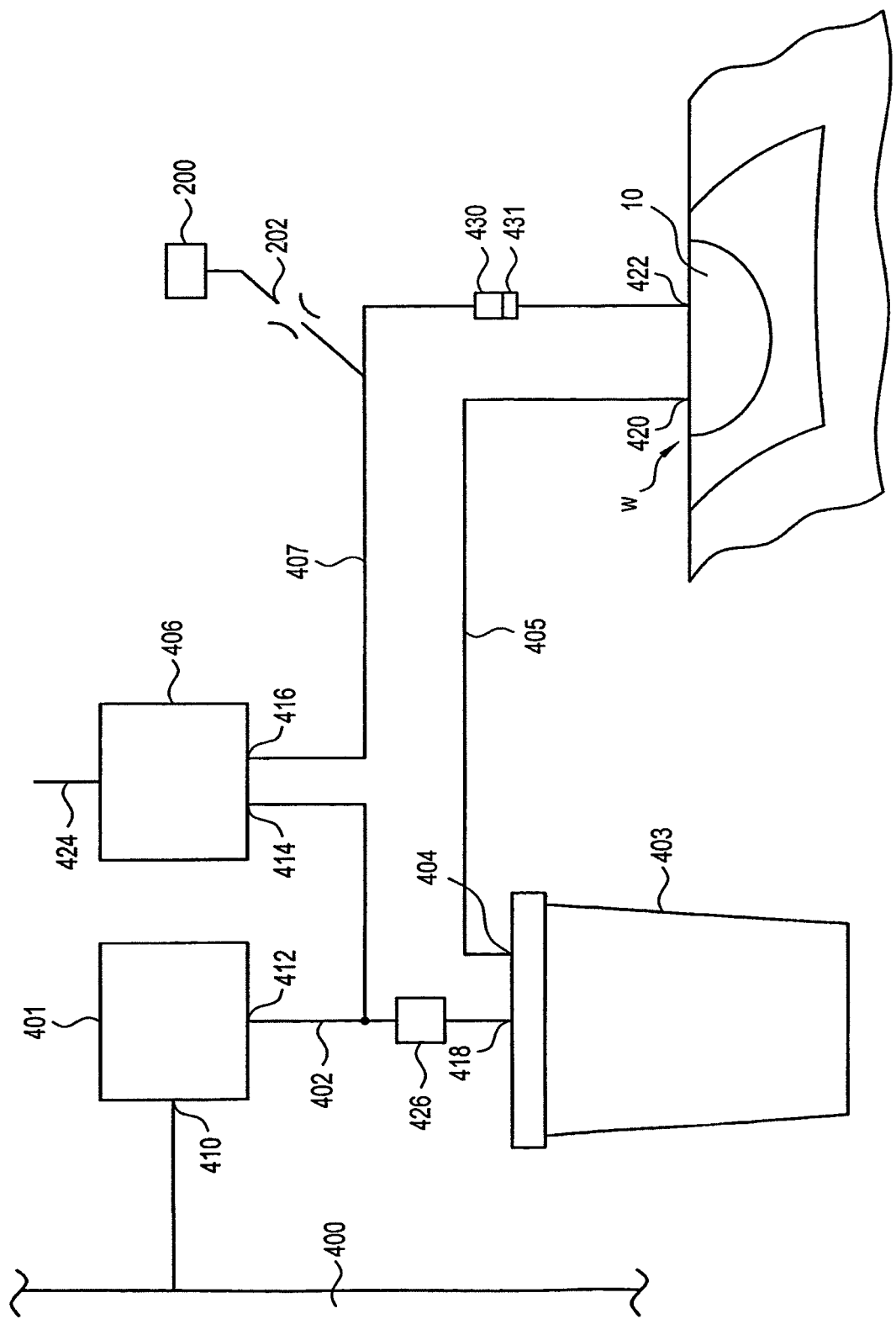
FIG. 10 is a diagram of a system for treating wounds with suction adapted to operate using in-house suction.

FIG. 10 illustrates a further exemplary system for treating wounds is shown incorporating an in-house vacuum source 400. This embodiment is primarily distinguished from previously disclosed embodiments by use of in-house suction source 400 in lieu of pump 20. As shown in FIG. 10, input port 410 of suction control (regulator) 401 is attached to a hospital wall suction system 400. Regulator 401 is capable of providing a regulated level of suction in the therapeutic range for wound drainage. Conduit 402 connects output port 412 of regulator 401 to suction port 418 of waste receptacle 403 and port 414 of leak detection sensor 406. Waste receptacle 403 also comprises another port 404 that is connected to wound W via conduit 405 and port 420 of suction delivery patch 10. Second port 422 is coupled to leak detection sensor 406 via conduit 407.

Optionally, a pressure difference measuring device, such as flow sensor 426, may be coupled between regulator 401 and wound cover 10. Flow sensor 426 may be any of various well-known types, such as a rotometer, a hot-wire anemometer, a mass flow sensor, differential pressure transducer, etc. Further, although flow meter 426 is illustrated adjacent an input of waste receptacle 403, the invention is not so limited in that flow meter 403 may be located at other points in the pneumatic circuit between regulator 401 and wound cover 10.

Leak detection sensor 406 compares the suction pressure applied to receptacle 403 to the actual suction pressure present in the wound space W. In one exemplary embodiment, leak detection sensor 406 is a differential pressure gauge. When no leak is present in the circuit and wound covering, the same pressure is applied to both sides of a diaphragm, thus, registering zero differential pressure and consequently no leak. As leaks are encountered, however, a lower pressure in the wound space occurs, resulting in a reduced pressure signal in conduit 407. In one exemplary embodiment, when this difference reaches a first predetermined level, such as 10% below the setting of regulator 401 for example, a signal may be provided to regulator 401, which in turn provides additional suction to port 418 of waste receptacle 403. In turn, when the difference is reduced to a second predetermined level, leak detection sensor 406 signals regulator 401 such that regulator 401 reduces the suction provided to waste receptacle 403. Further, differential pressures may desirably be calibrated to reflect an actual flow rate of a leak in the wound dressing. Further, similar to the exemplary embodiment of FIG. 9, filter/inlet 200 and restrictor 202 may be coupled to conduit 407.

In order to facilitate the accuracy of suction pressure measurements, it is necessary to keep conduit 407 clear of any trace amounts of fluids. It is recognized that slugs of fluid that are present in a pressure sensing line will impact the indicated pressure level. Fluids may enter the sensing conduit 407 through the ports adjacent the wound during any period where the suction is turned off or the system is disconnected from the patient. The system addresses this condition by allowing a small but controlled flow of air into conduit 407 via restrictor 202. This low flow serves to purge any slugs of fluid from conduit 407 when suction is applied to the wound. The flow through the restrictor also serves to indicate a non-obstructed condition when present. It is also important to filter the air using filter 200 to guard against the migration of microorganisms to the wound.

It will be recognized that it is not routine practice to disinfect hospital suction controls between each patient and it is necessary to guard against cross contamination of the patient by equipment. To that end, and to facilitate disconnecting of the system from the patient, a connector 430 in the sensing line 407 is employed. Connector 430 further employs a filter 431 that allows the passage of gas for pressure sensing, but is a barrier to fluids and microorganisms. Filter 431 functions to contain any wound fluids that could leak out of the conduit 407 and will preserve the cleanliness of the entire control. Flow through restrictor 202 can be adjusted to be sufficiently low so as to have minimal impact on the pressure reading, but still be effective in purging the line.

Although the connector 430 and filter 431 are described in conjunction with this particular embodiment, it will be recognized that they may also be used in any of the embodiments described herein as desired.

Measuring the flow of air as a means of determining the sealed condition of the wound has distinct advantages. When flow sensor 426 is placed downstream of waste receptacle 403, there is separation of fluids from air resulting in a non-contaminated line. Typical hospital collection containers incorporate filter-shutoff devices to guard against overflow and to protect the Hospital wall circuitry. In this manner, the sensor becomes isolated from patient fluids and reduces the risk of cross contamination. Also, it is readily possible to determine the suction level in the wound knowing the suction setting on regulator 401 and the leak rate determined by sensor 426. Thus, a simple, mechanical system is available to readily determine that a proper level of suction is selected and that the leak rate is sufficiently low as to provide a therapeutic level of suction to the wound.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for use with a source of suction for treating a wound of a patient with suction comprising:
    a cover having at least a portion which is conformable for covering the wound;
    an adhesive for sealing at least said portion of said cover to said the patient adjacent the wound;
    a pump;
    a first conduit coupled to and in fluid communication with said wound cover and said pump for applying suction to the wound and for carrying effluent from the wound for collection;
    a pressure sensor to monitor a level of suction within the wound;
    a second conduit coupled to and in fluid communication with said sensor and said wound cover;
    a controller for controlling the operation of said pump in response to a signal from said pressure sensor; and a passageway coupled to said second conduit for providing a rinsing flow of gas into said second conduit during operation of said pump to keep said second conduit free of effluent during the application of suction to the wound.

2. The system of claim 1 wherein said pump is arranged for applying suction up to a desired level to the wound and wherein said passageway is adapted for providing the flow of gas into said second conduit when the level of suction at the wound is at the desired level or some level below the desired level.

3. The system of claim 2 additionally comprising an internal power source for said pump.

4. The system of claim 2 wherein said adhesive is a pressure sensitive adhesive.

5. The system of claim 2 wherein said second conduit is smaller in diameter than said first conduit.

6. The system of claim 2 additionally comprising a reservoir having a portion arranged for receipt of effluent from the wound.

7. The system of claim 6 wherein said system is arranged to provide an alarm when the effluent in said portion of said reservoir has reached a predetermined level.

8. The system of claim 6 wherein said reservoir comprises a rigid canister.

9. The system of claim 2 wherein said pump is a positive displacement pump.

10. The system of claim 1 wherein at least a portion of said cover is liquid impermeable but moisture vapor permeable.

11. The system of claim 1 additionally comprising a minimally absorbent wound packing.

12. The system of claim 1 additionally comprising means for data logging operation of said system.

13. The system of claim 1 additionally comprising a suction delivery patch for coupling to said cover.

14. A system for use with a source of suction for treating a wound with suction and determining if an inadequate level of suction is being applied to the wound, said system comprising:
- a suction control for controlling the level of suction provided by the source of suction;
- a wound cover for enclosing the wound;
- a waste receptacle for collecting liquids from the wound and comprising an inlet and an outlet;
- a first conduit coupled between said source of suction and said outlet of said waste receptacle for producing a level of suction at said waste receptacle;
- a second conduit coupled between said waste receptacle and the wound for applying a level of suction to the wound;
- a third conduit connected in parallel to said second conduit and communicating with the wound;
- a pressure sensor for determining if there is difference in pressure between said first conduit and said third conduit; and
- a flow sensor coupled between the source of suction and said waste receptacle for sensing the flow of fluids to the source of suction.

15. The system of claim 14 wherein said pressure sensor is arranged for determining the difference in pressure between said first conduit and said third conduit and providing a signal representative thereof.

16. The system of claim 15 wherein said suction control is adapted to utilize the signal representative of the difference in pressure between said first conduit and said third conduit to control the level of suction provided by the source of suction.

17. The system of claim 14 additionally comprising a passageway coupled to said third conduit for providing a flow of gas into said third conduit, said flow of gas being operative to rinse effluent from said third conduit during the application of suction to the wound.

18. The system of claim 14 wherein said third conduit comprises a first portion and a second portion and wherein said system additionally comprises a connector located in said third conduit between said first and second portions.

19. The system of claim 14 additionally comprising a filter in fluid communication with said third conduit.

20. The system of claim 14 additionally comprising an adhesive for sealing at least said portion of said cover to the patient adjacent the wound.

21. The system of claim 14 additionally comprising a suction delivery patch.

22. The system of claim 19 additionally comprising a filter shut off.

23. A system for use with a source of suction for applying suction to a wound to treat the wound, wherein an obstructed condition of said system may result in an inadequate level of suction applied to the wound, said system being arranged for determining if an adequate level of suction is being applied to the wound and comprising:
- a cover for sealing the wound and thereby establishing a sealing state of the wound;
- a conduit in fluid communication with the source of suction and said wound cover for applying suction to the wound;
- a suction control for controlling the level of suction applied to the wound based upon a user selectable setting;
- a flow sensor for detecting the rate of flow of fluid in said conduit to determine the sealing state of the wound;
- a passageway in fluid communication with said conduit, said flow sensor and the ambient air outside of said system for providing a flow of air into said system; and
- wherein the detection of said flow of air by said flow sensor indicates a non-obstructed condition of said system.

24. The system of claim 23 wherein said flow sensor detects the rate of leakage of fluid into said system and wherein said system is arranged for determining if adequate suction is applied to the wound based upon the rate of leakage as detected by the sensor and said user selectable setting of said suction control.

25. The system of claim 23 additionally comprising a reservoir having a portion arranged for receipt of effluent from the wound.

26. The system of claim 23 wherein at least a portion of said cover is liquid impermeable but moisture vapor permeable.

27. The system of claim 23 wherein said passageway includes a flow restrictor.

* * * * *